United States Patent [19]
Gregory

[11] Patent Number: 6,117,128
[45] Date of Patent: Sep. 12, 2000

[54] ENERGY DELIVERY CATHETER AND METHOD FOR THE USE THEREOF

[75] Inventor: Kenton W. Gregory, 3737 SW. Council Crest Dr., Portland, Oreg. 97201

[73] Assignees: Kenton W. Gregory, Portland, Oreg.; Providence Health System, Seattle, Wash.

[21] Appl. No.: 09/070,895

[22] Filed: Apr. 30, 1998

Related U.S. Application Data

[60] Provisional application No. 60/088,363, Apr. 30, 1997.

[51] Int. Cl.[7] .................................................. A61B 18/18
[52] U.S. Cl. ................................... 606/7; 606/15; 607/89
[58] Field of Search .......................... 606/2, 7, 13, 14–16; 607/88, 89, 92, 93

[56] References Cited

U.S. PATENT DOCUMENTS

| | | |
|---|---|---|
| 3,582,187 | 6/1971 | Skillman . |
| 3,725,810 | 4/1973 | Ashkin et al. . |
| 3,920,980 | 11/1975 | Nath . |
| 4,045,119 | 8/1977 | Eastgate . |
| 4,729,621 | 3/1988 | Edelman . |
| 4,754,328 | 6/1988 | Barath et al. . |
| 4,768,858 | 9/1988 | Hussein . |
| 4,784,132 | 11/1988 | Fox et al. . |
| 4,800,876 | 1/1989 | Fox et al. . |
| 4,830,460 | 5/1989 | Goldenberg . |
| 4,832,444 | 5/1989 | Takahashi et al. . |
| 4,842,390 | 6/1989 | Sottini et al. . |
| 4,848,336 | 7/1989 | Fox et al. . |
| 4,878,893 | 11/1989 | Chin . |
| 4,913,505 | 4/1990 | Levy . |
| 5,005,944 | 4/1991 | Laakmann et al. . |
| 5,083,549 | 1/1992 | Cho et al. . |
| 5,165,773 | 11/1992 | Nath ......................................... 606/15 |
| 5,169,396 | 12/1992 | Dowlatshahi et al. . |
| 5,219,335 | 6/1993 | Willard et al. . |
| 5,267,341 | 11/1993 | Shearin ..................................... 606/15 |
| 5,292,305 | 3/1994 | Boudewijin et al. . |
| 5,400,789 | 3/1995 | Griffith . |
| 5,458,584 | 10/1995 | Ginn et al. . |
| 5,498,236 | 3/1996 | Dubrul et al. . |
| 5,571,151 | 11/1996 | Gregory . |
| 5,620,417 | 4/1997 | Jang et al. . |
| 5,709,676 | 1/1998 | Alt . |

OTHER PUBLICATIONS

Kenton W. Gregory and R. Rox Anderson, "Liquid Core Light Guide for Laser Angioplasty," *IEEE Journal of Quantum Electronics*, Dec. 1990, vol. 26, No. 12.

*Primary Examiner*—Michael Peffley
*Assistant Examiner*—Roy Gibson
*Attorney, Agent, or Firm*—Marger Johnson & McCollom, P.C.

[57] ABSTRACT

A catheter comprising a flexible tube having a proximal portion and a distal end portion. The proximal portion comprises a first or working lumen and a second lumen for a guidewire. The distal end portion consists of a small-diameter flexible tube having a single lumen. The catheter has a tapered transition portion interconnecting the proximal and distal portions, in which the first and second lumens have openings communicating internally of the catheter to the single lumen in the distal end portion. Coupled to a proximal end of the catheter are means for inserting an ultrasound or optical fiber into the first lumen for transmitting energy from an energy source through the catheter to an emission end near the distal end of the catheter and means for inserting the guidewire through the second lumen. The means for inserting are adapted to permit extension and retraction of the fiber and the guidewire in their respective lumens. The distal end portion containing the single lumen is sized to a diameter suitable for introduction into small cranial vessels, with an outer diameter less than that of the proximal portion containing the first and second lumens. This can be accomplished by sizing the distal end portion with an inner diameter of the single lumen just large enough to receive one of the guidewire and the fiber but not both.

29 Claims, 3 Drawing Sheets

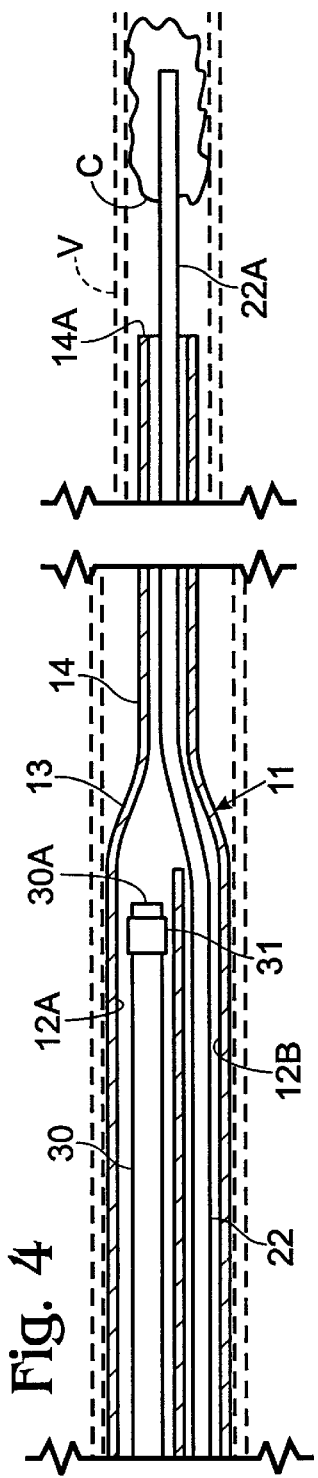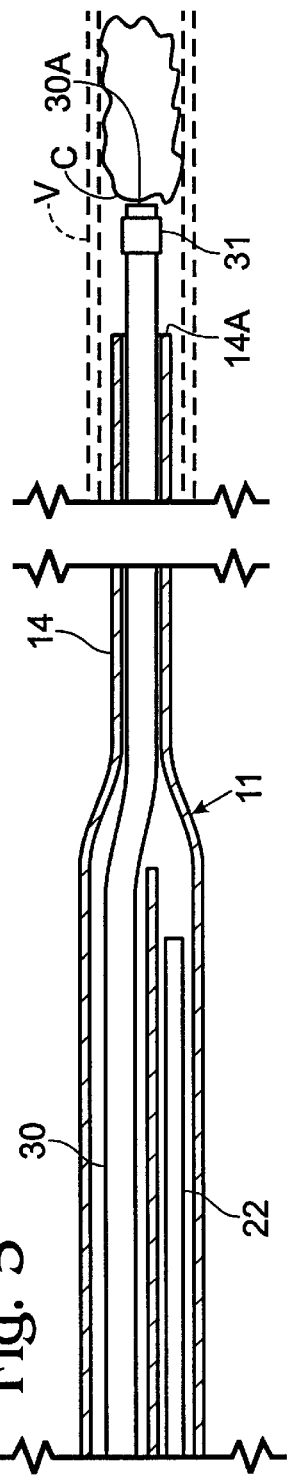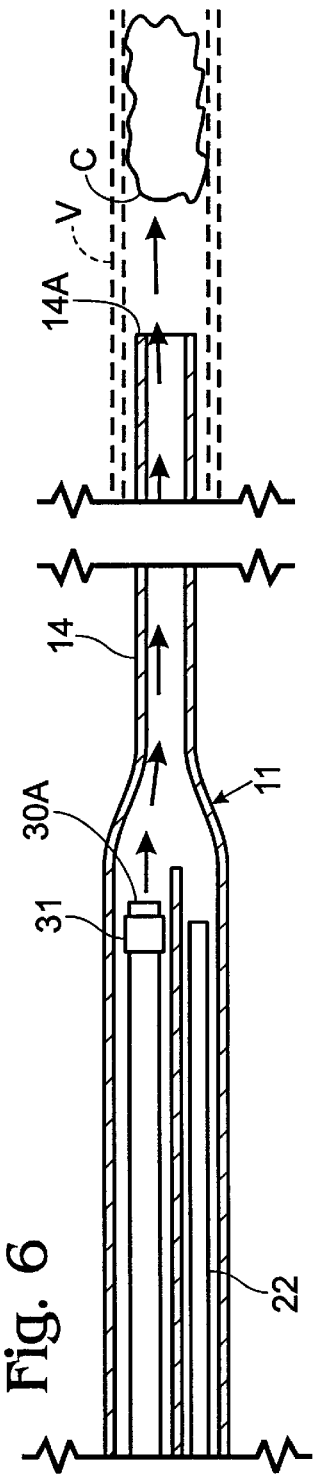

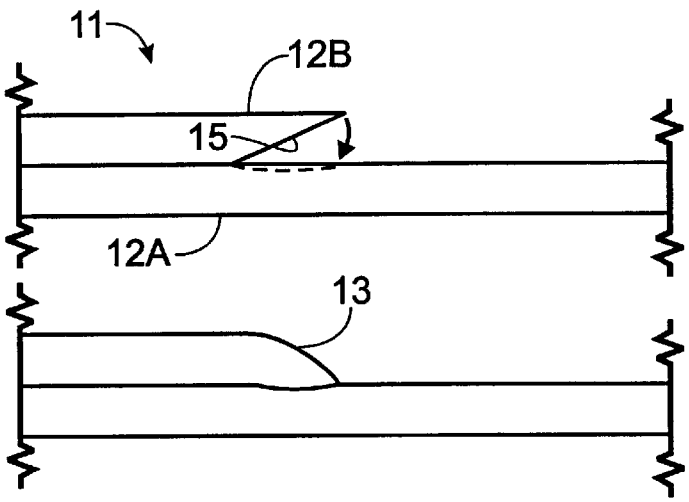
Fig. 7
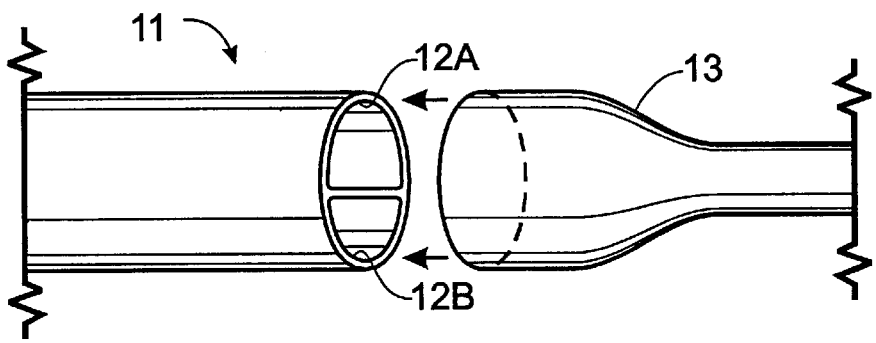
Fig. 8
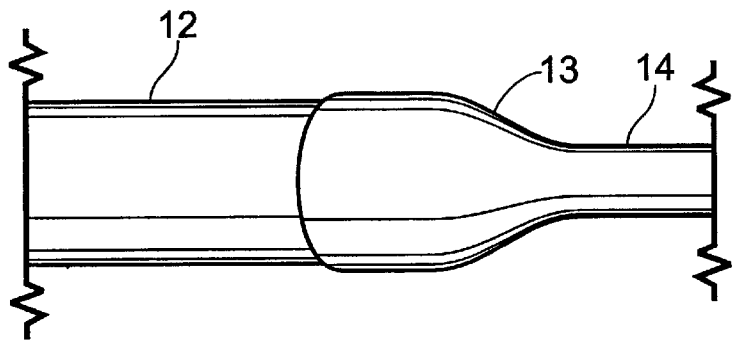
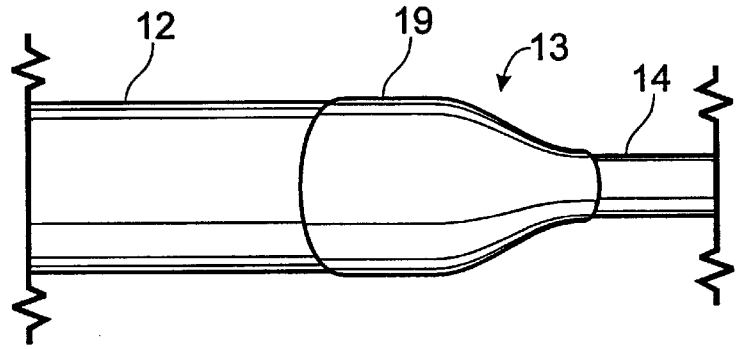
Fig. 9

ENERGY DELIVERY CATHETER AND METHOD FOR THE USE THEREOF

RELATED APPLICATION DATA

This application claims priority from provisional application, U.S. Ser. No. 60/088,363, filed Apr. 30, 1997, which is based on U.S. Ser. No. 08/846,426, filed Apr. 30, 1997, by Kenton W. Gregory, Robert Ziebol, and Mark Anders Rydell, for LIGHT DELIVERY CATHETER AND METHOD FOR THE USE THEREOF ("U.S. Ser. No. '426").

BACKGROUND OF THE INVENTION

1. Field of the Invention

The present invention relates to a method and apparatus for contemporaneous application of laser energy and localized delivery of pharmacologic therapy to a site within a body lumen and more particularly to a catheter adapted for localized treatment of vascular thrombosis disorders, for treatment and diagnosis of lumenal diseases particularly clots in the brain.

2. Description of Prior Art

Atherosclerosis, which is a major cause of cardiovascular disease, resulting in heart attacks, is characterized by the progressive accumulation of atherosclerotic deposits (known as plaque) on the inner walls of the arteries. As a result, blood flow is restricted and there is an increased likelihood of clot formation that can partially or completely block or occlude an artery, causing a heart attack. Arteries narrowed by atherosclerosis that cannot be treated effectively by drug therapy are typically treated by medical procedures designed to increase blood flow, including highly invasive procedures such as coronary artery bypass surgery and less invasive procedures such as balloon angioplasty, atherectomy and laser angioplasty.

Bypass surgery involves opening the patient's chest and transferring a vein cut from the patient's leg to the heart to construct a detour around the occluded artery. Bypass surgery requires prolonged hospitalization and an extensive recuperation period. Furthermore, bypass surgery also exposes the patient to a risk of major surgical complications.

Balloon angioplasty is a less invasive and less costly alternative to bypass surgery and is performed in a hospital cardiac catheterization laboratory by an interventional cardiologist. In this procedure, a balloon-tipped catheter is inserted into a blood vessel through a small incision in the patient's arm or leg. The physician uses a guide catheter to feed the balloon through the patient's blood vessels to the occluded artery. At that point, a guidewire is inserted across the deposits of atherosclerotic plaque, known as lesions, to provide a pathway for the balloon catheter. The deflated balloon is advanced over the guidewire, positioned within the occluded area and inflated and deflated several times. This inflation and deflation usually tears the plaque and expands the artery beyond its point of elastic recoil. Thus, although no plaque is removed, the opening through which blood flows is enlarged.

Atherectomy employs a rotating mechanical device mounted on a catheter to cut and remove plaque from a diseased artery. Although atherectomy, unlike balloon angioplasty, removes plaque from coronary arteries, existing atherectomy devices are not effective in treating certain types of lesions.

Laser angioplasty removes plaques by using light, in varying wavelengths ranging from ultraviolet to infrared, that is delivered to the lesion by a fiber optic catheter. Early attempts to develop a laser angioplasty system used continuous wave thermal lasers that generated heat to vaporize plaque. These laser systems caused charring and significant thermal damage to healthy tissue surrounding the lesion. As a result, thermal laser systems have generally been regarded as inappropriate for use in the coronary arteries. In contrast, excimer lasers use ultraviolet light to break the molecular bonds of atherosclerotic plaque, a process known as photoablation. Excimer lasers use electrically excited xenon and chloride gases to generate an ultraviolet laser pulse with a wavelength of 308 nanometers. This wavelength of ultraviolet light is absorbed by the proteins and lipids that comprise plaque, resulting in precise ablation of plaque and the restoration of blood flow without significant thermal damage to surrounding tissue. The ablated plaque is converted into carbon dioxide and other gases and minute particulate matter that can be easily eliminated.

In laser angioplasty, conventional light guides using fiber optics are used to direct laser energy onto arterial plaque formations to ablate the plaque or thrombus and remove the occlusion. Individual optically conducting fibers are typically made of fused silica or quartz, and are generally fairly inflexible unless they are very thin. A thin fiber flexible enough to pass through a lumen having curves of small radius, such as through arterial lumens from the femoral or the brachial artery to a coronary artery, typically projects a beam of laser energy of very small effective diameter, capable of producing only a very small opening in the occlusion. Small diameter fibers can mechanically perforate vessels when directed against the vessel wall as they are passed within the vessel toward the site.

In order to bring a sufficient quantity of energy from the laser to the thrombus or plaque, light guides proposed for use in laser angioplasty usually include a number of very thin fibers, each typically about 50 to 200 microns in diameter, bundled together or bound in a tubular matrix about a central lumen, forming a catheter. Laser energy emerging from a small number of fibers bundled together produces lumens of suboptimal diameter which can require subsequent enlargement by, for example, balloon dilation. Such devices do not always remove an adequate quantity of matter from the lesion, and their uses are generally limited to providing access for subsequent conventional balloon angioplasty.

Although individual fibers of such small dimensions are flexible enough to negotiate curves of fairly small radius, a bundle of even a few such fibers is less flexible and more costly. Coupling mechanisms for directing laser energy from the source into the individual fibers in a light guide made up of multiple small fibers can be complex. Improper launch of the laser energy into such a light guide can destroy the fibers. The directing of laser energy into arteries or veins thus far has been limited to two-dimensional imaging with fluoroscopy.

An alternative to conventional optical fiber technology using fused silica fibers or fiber bundles, is the use of fluid core light guides to transmit light into the body, as discussed by Gregory et al. in the article "Liquid Core Light Guide for Laser Angioplasty", *IEEE Journal of Quantum Electronics*, Vol. 26, No. 12, December 1990, and U.S. Pat. No. 5,304,171 to Gregory, incorporated herein. While fluid-core light guides may offer improvements of fused silica fibers or bundles, initial animal and clinical studies indicate inadequate or only partial removal of thrombus or atherosclerotic material, and a recurrence of atherosclerosis after treatment.

The foregoing techniques have been used with varying degrees of success in the treatment of coronary thrombosis.

In contrast, little has been done to alleviate the effects of blood clots in the brain. Techniques such as bypass surgery, balloon angioplasty, and atherectomy cannot be utilized in the brain. Laser angioplasty or thrombolysis has not offered much promise, because the small size and often tortuous configuration of blood vessels in the brain, through which the complex, relatively stiff and thick catheters required for laser angioplasty could not safely pass. Fluid core catheters used for coronary artery treatments require both a guidewire and a working laser or fiber optic channel. While more flexible than other catheters, such catheters are not sufficiently flexible to maneuver into cerebral vessels due to excessive catheter stiffness.

Another approach to treating thrombosis is to degrade thrombi by treatment with various pharmacologic agents. Many techniques currently exist for delivering medicant and other active agents to body tissue, These include: oral administration, direct injection into body tissue, and intravenous administration which involves introducing the active agent directly into the blood stream. These delivery mechanisms are systemic, in that they deliver the active agent via the bloodstream throughout the entire body. Effective pharmacologic or drug therapy requires achieving adequate concentrations of an active drug at the site of desired treatment without producing concentrations of the drug elsewhere in the body that create unwanted or dangerous side effects.

Workers in the field have discovered that many effective drugs which are capable of treating or curing disease cannot be effectively delivered systemically because the concentrations necessary for effective treatment produce adverse side effects in other parts of the body. For example, in the case of arterial and venous thrombosis, workers in the field have identified many potent agents which are capable of degrading thrombi, but clinical application of these agents has been limited by bleeding complications which can result in substantially increased morbidity and mortality. Moreover, even clinically approved agents such as streptokinase, urokinase, recombinant tissue plasminogen activators or even heparin have limited efficacy in treating acute myocardial infarction and other thrombotic disorders because they can produce systemic bleeding complications.

One approach to treating stroke that has been tried is to introduce a catheter arterially to the brain, into the region of a blood clot. The active agent is then infused in high concentrations and flowed by the thrombus. There are, however, practical limits to the duration of such treatment. Prolonged infusion will eventually produce a total accumulated systemic dose of the agent sufficient to create adverse side effects. Enzymatic degradation is in large part dependent upon the surface area of the thrombus which is exposed to the enzyme—which is limited to current infusion of enzymes which flow by the thrombus. In addition to the great cost of such an infusion, the prolonged indwelling of the catheter increases morbidity. The ability to administer an active agent locally to the thrombotic site without systemically affecting other tissues or creating complications, would greatly enhance the ability to effectively treat arterial and venous thrombus. Work to date has shown some benefits in reducing the effects of stroke but the results have not been dramatic. Blockage of blood flow to the brain cannot be withstood for a long enough time for pharmacologic treatment to be effective in many cases.

Accordingly, a need remains for a better method and apparatus for treating cerebral thrombosis.

SUMMARY OF THE INVENTION

The invention provides a catheter that is particularly adapted to use in the brain in the treatment of stroke, as well as a method for applying laser energy to the site of a clot in an intracranial vessel, and if desired to deliver contemporaneous pharmacologic therapy locally, using a liquid core laser catheter. The invention can also be used in combination with an imaging device such as ultrasound or optical coherence tomography fiber devices. In these cases, the distal lumen would preferably need to be transparent to the utilized frequencies of sound and light. An object of the invention is to provide a catheter that has improved flexibility and allows guidance by a guidewire to a site for conduct of a diagnostic or therapeutic procedure.

The catheter includes a flexible tube or tubes having a proximal portion and a distal end portion. The proximal portion comprises a first or working lumen and a second lumen for a guidewire. The distal end portion consists of a small-diameter flexible tube having a single lumen. The catheter has a tapered transition portion interconnecting the proximal and distal portions, in which the first and second lumens have openings communicating internally of the catheter to the single common lumen in the distal end portion. Coupled to a proximal end of the catheter are means for inserting an optical fiber or other device into the first lumen, and means for inserting the guidewire through the second lumen. The means for inserting are adapted to permit extension and retraction of the optical fiber and the guidewire in their respective lumens. The distal end portion containing the single lumen is sized to a diameter suitable for introduction into vessels, with an outer diameter less than that of the proximal portion containing the first and second lumens. This can be accomplished by sizing the distal end portion with an inner diameter of the single lumen large enough to receive one of the guidewire and the optical fiber but not both simultaneously.

In a preferred embodiment for the treatment of stroke, the catheter distal end portion can be sized to extend into small cranial vessels and with sufficient flexibility along its length to pass through tortuous vessel configurations such as a cavernous double turn. This arrangement avoids kinking or damage to the catheter tubing and reduces loss of light transmission effectiveness when used for laser thrombolysis or other applications of light through the catheter.

A fiber optical can be inserted through the first lumen for use in transmitting light or laser energy from an energy source through the catheter to an emission end near the distal end of the catheter. Preferably, for this application, the catheter proximal end includes means for coupling a flow of light transmissive liquid from an external source into the first lumen, to flow through the single lumen to form a fluid core light guide for laser energy launched from the optical fiber. The optical fiber need not extend through the single lumen to be used. The distal end portion of the catheter can have a sidewall capable of internally reflecting light into the liquid in the single lumen so that the liquid waveguides the laser energy from the emission end of the fiber through the single lumen to the site of a clot. An example of another device that can be inserted through the single lumen via the first lumen is an ultrasound transducer for use in intravascular imagings, or other means for transmitting therapeutic or diagnostic energies,. In this application, the distal end portion need not be internally reflective, and a flow of light transmissive liquid is not essential although other liquids can be used.

A method according to the invention for using the catheter comprises the steps of inserting the catheter through a blood vessel until the distal end portion is proximate a selected site, such as the site of a clot to be treated, guided by a guided wire extending through the second lumen and the single lumen. Then, the guidewire is retracted from the single lumen to back its distal end into the second lumen. This step clears an open pathway through the single lumen for either the optical fiber to be advanced therethrough or for laser energy to be launched through a fluid core light guiding stream. The foregoing method steps can be repeated, advancing the distal end portion of the catheter through the vessel as the clot is dispersed, by extending the guidewire, advancing the catheter along the guidewire, and again retracting the guidewire to make way for the optical fiber or a beam of laser energy or other device to pass through the single lumen. Alternatively, in the same way but for diagnostic applications, a device such as an ultrasound imaging transducer can be advanced through the first lumen and single lumen to the selected site after the guidewire has been retracted for imaging without the interference of the guidewire in the lumen.

The method can also include preparing a dose of pharmacologic agent, introducing the dose of pharmacologic agent into the light transmissive liquid or other liquid, directing the catheter distal end to the site, and flowing the liquid containing the pharmacologic agent through the catheter for discharge at the distal end into the vessel adjacent the site contemporaneously with light or laser energy delivery via the single lumen through the liquid. The term "contemporaneously" means during or proximately before or after, as applicable to the treatment. Using a liquid core laser catheter for treatment of thrombosis can thereby be augmented by the additional administration of high-dose pharmacologic therapies at the site contemporaneous with the discharge of light energy from the catheter to help remove residual thrombus or prevent recurrence of thrombosis, or to treat the tissue in the region of the thrombus after its removal.

The foregoing and other objects, features and advantages of the invention will become more readily apparent from the following detailed description of a preferred embodiment of the invention which proceeds with reference to the accompanying drawings.

BRIEF DESCRIPTION OF THE DRAWINGS

FIG. 4 is a lengthwise sectional view of the distal end portion of the catheter of FIG. 1 shown in an arterial lumen (shown in dashed lines) in proximity to a blood clot, with the guidewire extended through the distal end portion of the catheter and the optical fiber retracted.

FIG. 5 is a lengthwise sectional view similar to FIG. 4, with the guidewire retracted and the optical fiber extended for treating the clot.

FIG. 6 is a lengthwise sectional view similar to FIG. 4, with both the guidewire and the optical fiber retracted for transmitting laser energy through the distal end portion of the catheter via a fluid stream to the treatment site.

FIG. 7 is a lengthwise sectional view of a preferred transition portion from the proximal portion of the catheter to the distal portion.

FIG. 8 is a perspective view of an alternate embodiment of the transition portion between the proximal portion of the catheter to the distal portion.

FIG. 9 is a side elevation view of another alternate embodiment of the transition portion between the proximal portion of the catheter to the distal portion.

DETAILED DESCRIPTION

The catheter device of the present invention is designed for accessing lumenal structures requiring a guidewire for support and atraumatic guidance. It is an improvement over present guidewire-directed catheters used for laser energy delivery (particularly over monorail type devices) as it provides the maximum lumen for maximum laser spot size but minimizes overall outside diameter and stiffness of the distal catheter to enable it to be placed in smaller more tortuous vessels, such as those of the brain. It also allows guidewire directed catheter passage but then allows for convenient wire removal during laser energy delivery or other interventions where the guidewire would interfere with such interventions.

The catheter is basically composed of two lumens terminating into a single lumen with the single distal lumen being accessible internally by either the wire or an optical fiber. The lumens open internally into the single common distal lumen. This catheter is particularly important for fluid core light guide delivery via the optical channel.

This catheter would also be a potential improvement for intravascular ultrasound imaging and optical coherence tomography and other devices that require a small, flexible working channel that can be brought to the desired location in the body with a guidewire and then have the guidewire easily removed, leaving the distal working channel free for use of the diagnostic or therapeutic technology to be used rather than using laser fibers through the working channel.

Figure 1:
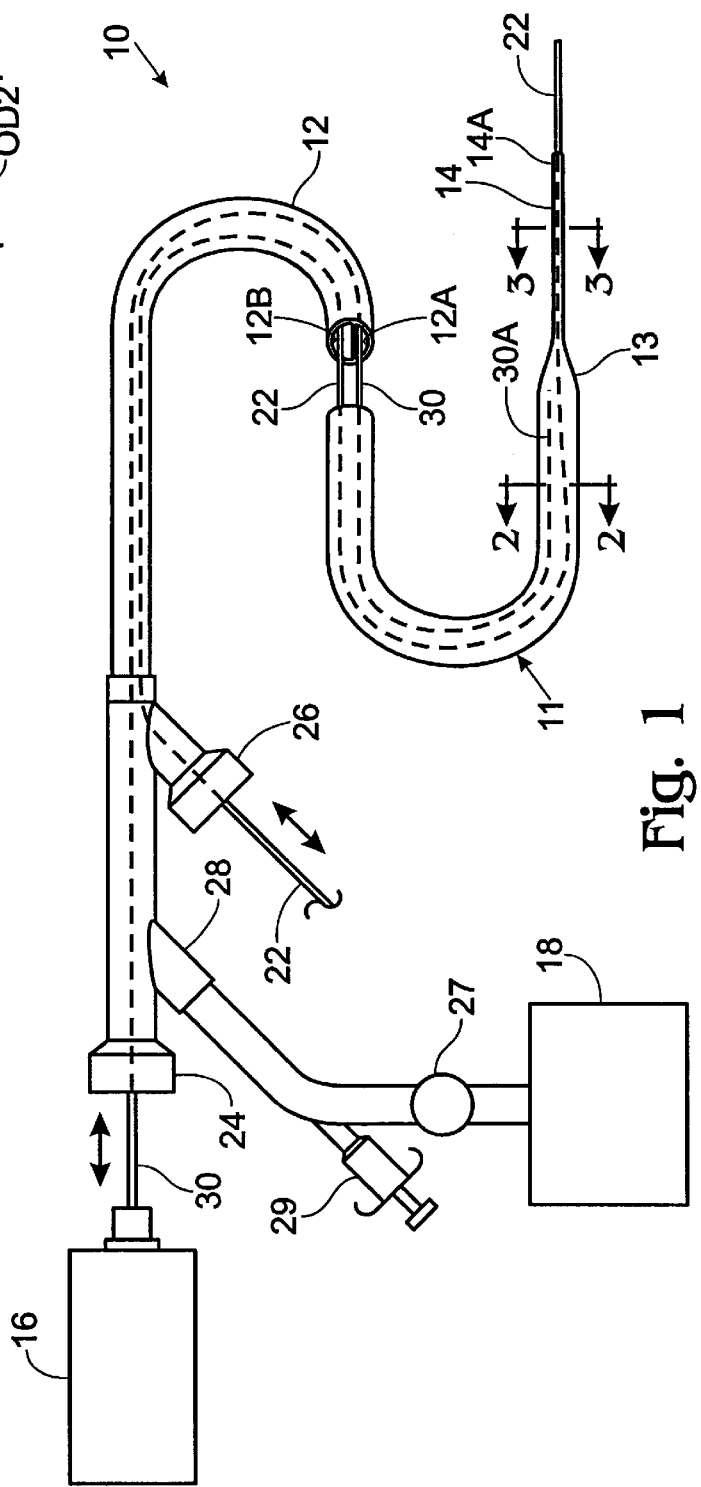
FIG. 1 is a schematic diagram of a liquid core laser drug delivery system including a catheter according to the present invention, with a guidewire extended through the distal end portion of the catheter.

FIG. 1 illustrates the liquid core laser drug delivery system 10 of the present invention, shown in schematic form, and the catheter 11 of the present invention is shown in further detail in FIGS. 2–6. In general terms, system 10 comprises a catheter 11 having a proximal portion 12 of a first diameter OD1 and flexibility and a smaller outer diameter OD2, more flexible distal end portion 14 for insertion into a lumen, such as a blood vessel V. The distal end portion 14 is a small-diameter (OD2) flexible tube consisting of a single lumen. The catheter 11 has a tapered transition portion 13 interconnecting the proximal and distal portions 12, 14, in which the first and second lumens 12A, 12B have openings communicating internally of the catheter to the single lumen in the distal end portion 14. Such transition portion 13 is described in more detail below with reference to FIGS. 7–9.

Figure 3:
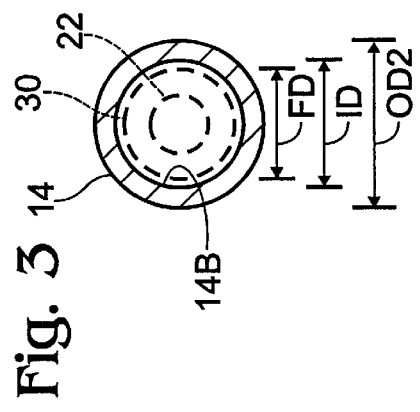
FIG. 3 is a cross-sectional view taken along lines 3—3 of FIG. 1.
Figure 2:
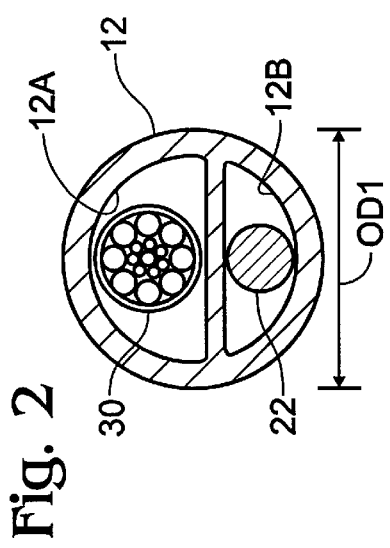
FIG. 2 is a cross-sectional view taken along lines 2—2 of FIG. 1.

Referring to FIGS. 3 and 4, the distal end portion 14 containing the single lumen is sized to an outside diameter suitable for introduction into a vessel V. The single lumen of the distal end portion 14 has an outside diameter OD2 less than the outside diameter OD1 of the proximal portion containing the first and second lumens 12A, 12B. As shown in FIG. 2, the first and second lumens 12A, 12B are sized to preferably admit an optical fiber bundle 30 and a guidewire 22, respectively. The distal end portion has an inner diameter ID in the single lumen just large enough to receive one of the guidewire and the optical fiber, diameter FD, but not both simultaneously.

Coupled to the proximal end of the catheter are means 24 for inserting an optical fiber (or other device) retractably into the first lumen 12A, and means 26 for inserting the guidewire through the second lumen 12B. An external source 16 of laser energy is coupled to optical fiber 30. The working lumen 12A is proximally terminated by an o-ring, Y type adapter where the o-ring connector is maintained for passage of an optical fiber or fiber bundle 30 that is coupled to a laser 16 for laser energy delivery. The y-connector 28 is connected to a fluid reservoir 18 and pumping device 29 as described in U.S. Pat. No. 5,304,171 to input to one of the proximal lumens of the catheter 11 a flow of light transmissive liquid having a suitable index of refraction and a dose from an external source 29 of an active pharmacologic agent. The preferred means for inserting are adapted by use of o-ring couplings or similar sealing devices to permit extension and retraction of the optical fiber 30 and the guidewire 22 in their respective lumens.

The catheter distal end portion 14 has a sidewall which has either a reflective internal surface (e.g., a metal coating) or suitably low index of refraction compared to the light transmissive liquid to allow internal reflection of light through which the liquid flows. The tapered transition portion 13 can be formed of the same material as the distal end portion 14. Optionally, one or both of the proximal lumens can be formed with the same sidewall coating or materials as used for the distal end portion.

For non-fluid core catheter device applications, the catheter is similarly constructed but without the need for an internally reflecting material or medium. The guidewire channel and guidewire would be similarly utilized. The second (working) lumen would house, for example, an ultrasound or optical coherence tomography fiber device that can be advanced safely distally within the single (common) lumen. In these cases, the distal portion of the catheter would need to be transparent to the utilized frequencies of sound or light rather than internally reflective as noted in the previous fluid core laser catheter embodiment. The device would be positioned distally within the catheter distal end portion or extended beyond it for vascular imaging without having the guidewire present which would degrade the imaging signal. Once the imaging is accomplished, the imaging device is withdrawn into the proximal working lumen 12A from the common distal lumen and the guidewire re-advanced into the distal lumen and beyond for re-positioning the catheter and device into another portion of the same or another vessel.

Catheter-based ultrasound is used for diagnosis and treatment of lumenal structures including arteries and ureters. Ultrasound energy can be generated outside the body and transmitted to the desired location in the body at the catheter tip or ultrasound energy can be generated at the catheter tip usually via a piezo-electric crystal mounted on a fixed or rotating device at the catheter tip. Such catheters are referred to herein as including fiber-based transducers as the energy source. Lower energy ultrasound energy can be transmitted and received for imaging while higher energy can be used for oblation of thrombi, atherosclerotic lesions or stones.

In each case of all ultrasound catheters, passage into the desired lumenal location requires a guidewire and catheter assembly for positioning the ultrasound catheter. In each case, once the catheter is in the desired location, the presence of a guidewire at or near the site of ultrasound energy delivery interferes with the intended diagnostic or therapeutic effect of the ultrasound catheter and guidewire removal is required for optimal performance of the procedure.

The second lumen 12B is provided for the guidewire 22 and is terminated proximally in an opening that will allow introduction and passage of a guidewire. Distally, lumen 12B terminates adjacent the transition portion 13. The guidewire lumen 12B opens internally of the catheter into the common single lumen of distal end portion 14 for passage of the wire into the vessel of the body for safe advancement and guiding of the entire catheter. The guidewire lumen can be made of any medical plastic or material and does not require light guiding properties. It simply must satisfy strength and flexibility requirements that are well known and commonplace in vascular catheters.

The guidewire lumen proximal termination is preferably via an o-ring-Y adapter 26 so that the o-ring lumen will allow the guide wire to slide in and out, and can be closed so that fluid under pressure from the bloodstream and the pressure injector will not leak backwards. The Y channel can also be used to flush the guidewire lumen or provide additional optical fluid flow to the common distal channel if sufficient flow through the optical channel of lumen 12A around fiber 30 cannot be accomplished. The particular structure of the coupling means 24, 26, 28 is not important to the invention; any structure will suffice that enables sliding extension and retraction of a guidewire and an optical fiber or other fiber-like device, and the introduction of the fluids need for the particular procedure.

Radio-opaque markers should be placed at important catheter locations to allow the operator to maximize the safe use of the properties of this catheter system. Markers should be placed at the distal tip of the common lumen as they are on many catheters for vascular use. Additionally, the optical fiber tip should have a radio-opaque marker 31 to ensure adequate placement. Similarly, the guidewire tip should have a marker. Preferably, the transition 13 from dual to single lumen would also have a means of identifying the transition point with a radio-opaque marker, or the entire distal end portion 14 can be impregnated with a radio-opaque material.

The catheter 11, with two lumens 12A, 12B opening internally into a common lumen of a distal end portion via a tapered transition portion 13, can be made a number of ways. As illustrated in FIG. 7, one way is to coextrude two tubings, cut away the distal end of one tube preferably on a diagonal slice 15 at an acute angle to the second tubing and splice the resulting end into an opening 17 in the other tubing (shown by dashed lines in FIG. 7). The distal end of one tube can also be cut away at an obtuse angle adjacent the opening in the other tubing and a patch heat shrunk over the cut to yield only an internal communication between the first tube and the second. The distal end portion forming the common lumen can simply be an extension of one of the first or second lumens of the proximal portion of catheter 11 or be an attached lumen (as in FIGS. 8 and 9) of the same or differing material depending on the application of the catheter.

An alternate method for forming the tapered transition portion 13 is illustrated in FIG. 8 where a stretched or heat expanded end of the single lumen 14 is glued or otherwise fused to the outside surface of the coextruded dual lumen 12. A further alternate method for forming the tapered transition portion 13 is illustrated in FIG. 9 where a discrete connector is heat shrunk across the terminus adjacent proximal and distal lumens 12 and 14.

The materials used for the catheter sidewall and for the light transmissive liquid are selected based in part to provide a high degree of internal reflection at the conduit surface to provide an energy guide for laser or ultrasound applications. Specifically, the catheter sidewall and liquid are each transparent to laser energy which is conducted through the distal lumen while the index of refraction $N_w$ of the side wall is less than the index of refraction $N_f$ of the liquid. Further, the material used to construct the sidewall of the catheter is also selected in part to provide structural strength as well as flexibility so that the distal end portion 14 can be bent through curves of small radii without kinking or substantially distorting the cross sectional geometry of the distal lumen. I prefer to make the catheter sidewall out of a fluorinated ethylenepropylene material which is available commercially, for example, as FEP Teflon® a DuPont product, THV—tetrafloroethylene hexafloropropylene and vanillidine floride, a 3M product, or to use a coating of suitably low index-of-refraction optical media. If an internal metallized reflective surface coating is used, the sidewall need not be optically transparent for laser applications and the proximal lumens can be formed by any medical grade plastic material of sufficient strength and flexibility such as medical grade PET or PVC.

For non-high energy light propagation DIL applications such as intravascular ultrasound or intravascular OCT, the second (working) channel of the proximal lumen and common single (common) channel of the distal lumen require only that the tubing material only be transparent to the incident radiation frequency. For non-imaging applications, the catheter material should only require sufficient strength and flexibility and be of appropriate biocompatibility for temporary insertion into vessels or other locations in the body.

The light transmissive liquid is injectable, transparent in laser wavelengths, and has a refractive index greater than the refractive index of the catheter sidewall. Suitable liquids include solutions of sugars such as mannitol, glucose, dextrose, and iodinated contrast media. A solution having a refractive index of about 1.4 is preferred. For example, FEP Teflon® has a refractive index of about 1.33, thus, the ratio of refractive indices relative to such solutions is approximately 1.1. A ratio of 1.1 provides for substantially total internal reflection even at fairly steep angles of incidence. The interior surface of the catheter sidewall should be smooth; surface roughness can produce unsatisfactory irregularities in angle of incidence.

The overall length of the catheter 11 can range from 100 to 180 cm, and preferably 120–140 cm., for treatment of humans. The diameter of the working lumen 12A will vary depending on the clinical application and the size of the vessel that is desired to be accessed but generally varying between 300 and 2000 microns and most commonly between 400 and 1500 microns. The guidewire lumen 12B should be large enough to accommodate conventional guidewires (having an outside diameter of between approximately 254 to 965 microns) so that the guidewire lumen inside diameter should be at least approximately 355 to 1270 microns. The guidewire lumen can also be coated with a slippery material to reduce resistance and enhance guidewire passage.

The distal end portion 14 generally has an inside diameter (ID) sufficient for at least the guidewire to extend through the common lumen (about 350 to 3000 microns). The thickness of the catheter sidewall 121 is generally less than 254 microns. The distal lumen length can vary between 1 cm and 50 cm but optimally, between 1 and 40 cm and preferably between 5 and 20 cm. This length can be varied depending upon the path through which the catheter is expected to travel. For instance, when a catheter constructed according to the invention is used to treat blood clots in the brain, the catheter is typically maneuvered through the cerebral vessels in the neck and into the brain. This path includes a cavernous double turn through which thicker catheters, such as one containing dual lumens, cannot pass. Thus, the distal portion of the catheter of the present invention would have a sufficient length so that it can reach the occlusion with the thicker proximal portion of the catheter positioned outside of this turn. The inside diameter of the lumen will vary between 300 and 1500 microns, preferably between 400 and 1200 microns and will taper from the dual lumen dimension to enhance catheter movement and reduce kinking of the catheter which would diminish light propagation.

OPERATION

The liquid core laser drug delivery system 10 operates generally as follows, with specific reference to its use for ablating and pharmacologically treating arteries or veins occluded by thrombus. It is understood, however, that the invention can operate for the diagnosis and treatment of other luminal diseases. To operate the invention according to a preferred method, fill catheter 11 with liquid, and then couple a source 18 of liquid to the proximal end of conduit 24. Introduce the liquid-filled conduit 24, distal end first, through an opening in the skin and through the wall of a large artery. Then direct the catheter toward the selected site, until the distal end 14 is directed toward the occlusion. Then activate the laser energy source 16 to produce laser energy having the desired wavelength, pulse duration and intervals. When the ablation and drug delivery are completed, withdraw the liquid-filled catheter from the lumen.

Guidewire 22 is used to position the distal end 14 of catheter 12 adjacent the selected site, such as clot C in vessel V in FIG. 4. Once the catheter is safely guided into the desired location in the body, the guidewire can be withdrawn from the common distal lumen into the guidewire lumen but not completely out of the entire catheter. Once the guidewire is "parked" the optical fiber can be advanced into the common lumen (as in FIG. 5) or fired from its own lumen without having the guidewire obstructing and interfering with optical fluid and light flow (as in FIG. 6). Once the distal end 14 is positioned adjacent the site C, introduce light transmissive liquid and then direct and couple laser energy from a source of laser energy 16 into the proximal end of optical fiber 30. Fiber 30 launches the laser energy into the liquid, which conveys the energy through distal end portion 14 to the clot.

The procedure employing catheter 11 for vascular use can be summarized as follows:

Place guiding catheter proximal to desired vessel.

Flush both lumens of catheter 11.

Place guidewire 22 in guidewire lumen 12B with or without optical fiber placement.

Advance guidewire 22 out past common lumen tip 14A into the vessel V and pass catheter 11 over guidewire, positioning it into the desired location via fluoroscopic and standard angioplasty techniques.

Retract the guidewire 22 into its lumen 12B proximally past the common distal lumen.

Advance the optical fiber(s) through the working lumen 12A into the desired position either within its lumen or into the distal common lumen.

Flush catheter system if needed and confirm angiographically via tip markers the appropriate location of each component.

Begin optical fluid flow via the fluid injector.

Fire laser.

Repeat these steps to replace catheter into another location by withdrawing the optical fiber into its channel (if it had been advanced into the distal common lumen) and advancing guidewire from its parked position into the desired vascular location. Advance the catheter 11 over the guidewire and confirm location. Advance the optical assembly if necessary and fill the optical channel with optical fluid (usually iodinate radiographic contrast media). Fire the laser when contrast is visualized angiographically.

The proportion of the energy introduced into the liquid that emerges from the distal end 14A of the common lumen depends upon the dimensions and physical characteristics of the liquid and upon the conduit sidewall, and on the extent to which the catheter 11, and particularly the end portion 14, follows a curving course.

Optionally, either before or after I activate the laser energy source, I introduce the active agent in solution from the source of active agent 18 into the stream of flowing liquid 60 by depressing syringe 20. The emission end 30A of the optical fiber 30 can be positioned near (plus/minus ~2 mm.) the distal end 14A of the catheter 11 for launching the light directly into the fluid at the end of the catheter. The optical fiber can be selectively positioned away from or near the distal end of the catheter, as shown in FIGS. 5 and 6, respectively or anywhere in between, to modulate the light intensity and beam diameter emitted from the catheter. If the catheter is only used with the end 30A of the fiber near the end 14A of the catheter, the inner sidewall of the distal end portion catheter need not be internally reflective. I prefer to launch laser energy from the optical fiber 30 into the fluid stream at a distance from the tip of catheter 11 to a position ranging about 20 cm withdrawn from the distal end 14. Experimentation has shown that each internal reflection of the laser energy within the catheter decreases the beam energy by approximately ten percent. Accordingly, the shorter the distance from the launch point to the distal end of the catheter, the higher the percentage transmission of laser energy.

A pharmacologic agent can be either added directly to the liquid source 18 or optionally a dose can be kept ready in syringe 29 or other means of injecting a prescribed volume or amount of the agent into the optical stream. Virtually any concentration of pharmacologic agent in solution can be used depending upon the desired medical effect. For example, in the treatment of intravascular thrombosis urokinase 250–1,000,000 units, streptokinase 250–1,000,000 units, recombinant tissue plasminogen activator 25–150 mg, heparin 2500–10,000 units, hirudin, argotropin, hirulog or other anticoagulants, gene products, enzymes, antiplatelet agents, anti-proliferative agents or combinations thereof can be added to the optical fluid. Other agents that are also deployed to combat thrombosis or its sequelae could also be added to the fluid as long as such agents do not decrease the ability to transmit light through the fluid. The treatment of thrombosis is only one of the many medical uses for this invention.

Having described and illustrated the principles of the invention in a preferred embodiment thereof, it should be apparent that the invention can be modified in arrangement and detail without departing from such principles. I claim all modifications and variations coming within the spirit and scope of the following claims.

What is claimed is:

1. A light energy delivery catheter comprising:
   a proximal portion having first and second lumens extending therethrough;
   a distal portion having a single lumen extending therethrough; and
   a short tapered section interconnecting the proximal and distal portions, said first and second lumens being adapted to receive a guidewire and a light energy guide respectively, said first and second lumens opening internally into said single lumen to permit either the guidewire in said first lumen or the light energy guide in said second lumen to extend into said single lumen in the distal portion, the single lumen being internally reflective to light energy introduced via the light energy guide.

2. A catheter as claimed in claim 1 including a port defined in the proximal portion through which optical or radiographic contrast fluid is applied to flow through one of the said first or second lumens and out through said single lumen.

3. A catheter as claimed in claim 2 wherein said distal portion is formed of a material having a refractive index which is less than that of the contrast fluid.

4. A catheter as claimed in claim 3 wherein the distal portion is formed of a floropolymer material.

5. A catheter as claimed in claim 1 including an optical light energy guide received in said second lumen.

6. A catheter as claimed in claim 1 including a guiderwire in said first lumen.

7. A catheter as claimed in claim 1 wherein a reflective cladding is applied internally to the single lumen of the distal portion.

8. A method for directing light energy therapeutically to a site within a blood vessel of the brain, the method utilizing a catheter having a proximal portion with a first and second lumen extending therethrough, which is attached to a distal portion having a single lumen opening internally into the first and second lumens, a guidewire in said first lumen and a coupled to a light energy guide in said second lumen, and a fluid introduction means for introducing a fluid to the proximal portion, the method comprising the steps of:
   inserting the catheter through the blood vessel in the brain;
   extending the guidewire through the first lumen and into the single lumen;
   guiding the catheter using the guidewire until an end of the distal portion is adjacent the site;
   retracting the guidewire from the single lumen and into the first lumen to clear the single lumen of obstruction;
   advancing a distal end of the light energy guide partway into the single lumen;
   flowing optical fluid through the catheter for discharge adjacent the site at the end of the distal portion; and
   transmitting light energy from said light energy source through the light energy guide and through the single lumen via the optical fluid to said site, the inner surface of said single lumen being internally reflective to the light energy to guide the light energy from the distal end of the light energy guide to the site, unobstructed by the guidewire.

9. The method of claim 8, further including transmitting light energy from said energy source through said second lumen and to said site contemporaneously with flowing a dose of the pharmacological agent to the site from a drug source coupled to one of the first and second lumens.

10. The method of claim 8, wherein said light energy source is a laser.

11. The method as claimed in claim 8, further including:
   retracting the light guide from the single lumen so that it is fully within said second lumen and advancing the guidewire through the single lumen to extend from the distal end thereof;
   using the guidewire to reposition the distal end of the catheter relative to a clot in the blood vessel; and repeating the advancing, flowing and transmitting steps as necessary for treatment.

12. A method for removing a blood clot in the brain, the method utilizing a light delivery catheter having a proximal portion with a first and second lumen extending therethrough, which is attached to a distal portion having a single lumen opening internally into the first and second lumens, a guidewire in said first lumen and a light guide having a distal end in said second lumen, the method comprising:

(a) inserting said catheter into an artery in the brain with the guidewire extending through said single lumen and out a short distance from the distal end of the catheter, and utilizing said guidewire to advance the catheter to the clot;

(b) retracting the guidewire from the single lumen so that it is fully within said first lumen, (c) advancing the light guide into the single lumen to position the distal end thereof partway into the single lumen; and (d) applying light energy through the light guide and single lumen to the clot.

13. A method as claimed in claim 1 including the step performed before and during step (d) of flowing a contrast fluid through said second lumen and said single lumen to the clot to conduct the light energy through the single lumen and the vessel to the clot.

14. A method as claimed in claim 12 including the steps performed after step (d) of:

(e) retracting the light guide from the single lumen so that it is fully within said second lumen and advancing the guidewire through the single lumen to extend from the distal end thereof;

(f) using the guidewire to reposition the catheter relative to the clot; and (g) repeating steps (b), (c) and (d).

15. A method as claimed in claim 12 including the step performed after each performance of step (d) of:

(e) terminating step (d) and flowing a thrombolytic drug through one of the first or second lumens and the single lumen to the clot.

16. The method as claimed in claim 12 in which step (d) includes flowing an optical fluid through one of the first and second lumens, through the single lumen and out the distal end to transmit the light energy to the clot.

17. A catheter assembly for treating blood clots formed in a vessel in the brain comprising:

a flexible tube having a proximal portion and a distal portion, said proximal portion comprising a first lumen and a second lumen and said distal portion forming a single lumen communicating with said first and second lumens;

a guidewire received in said first lumen and retractably received in said single lumen for guiding said catheter into a vessel to position a distal end of the single lumen adjacent a blood clot;

a light energy source coupled to the second lumen; and light energy transmission means within the second lumen for transmitting light energy from said light energy source to the distal portion of the flexible tube;

the distal portion being internally reflective to guide the light energy though the single lumen to the clot.

18. A catheter as claimed in claim 17 wherein said distal portion is flexible.

19. A catheter as claimed in claim 17 wherein the distal portion is tapered to enhance flexibility.

20. A catheter as claimed in claim 17 wherein said distal portion is approximately 1 to 50 cm long.

21. A catheter as claimed in claim 17 wherein said distal portion is approximately 1 to 40 cm long.

22. A catheter as claimed in claim 17 wherein said distal portion is approximately 5 to 20 cm long.

23. The catheter assembly according to claim 17 wherein said energy source includes a laser.

24. The catheter assembly according to claim 23 wherein the energy transmission means includes a light transmissive liquid forming a light wave guide in the distal portion.

25. The catheter assembly according to claim 23 wherein the energy transmission means includes at least one optical fiber.

26. The catheter assembly according to claim 17, further including means for introducing a pharmacological agent into the single lumen for discharge into the vessel adjacent the blood clot contemporaneously with the transmission of energy out the distal portion of the flexible tube.

27. The catheter assembly described in claim 17, further including fluid introduction means for flowing fluid through at least one of the proximal lumens and through the single lumen.

28. The catheter assembly for treating blood clots formed in a vessel in the brain as claimed in claim 17, wherein a tapered transition junction permits the joining of:

a distal portion subassembly sized and arranged to extend into a small, tortuous cranial vessel and for propagation of the light energy from the said light energy source to the blood clot; and a proximal portion subassembly particularly suited for the accommodation of the light energy transmission means within the second lumen to convey light energy into the distal portion subassembly.

29. The catheter assembly for treating blood clots formed in a vessel in the brain as claimed in claim 17, wherein said light energy transmission means includes means for introducing optical fluid through one of the first and second lumens, through the single lumen and out the distal end to transmit the light energy to the clot.

* * * * *